US00PP17798P2

(12) United States Plant Patent
Oudshoorn

(10) Patent No.: US PP17,798 P2
(45) Date of Patent: Jun. 12, 2007

(54) ***PHYGELIUS* PLANT NAMED 'PASSIONATE'**

(50) Latin Name: *Phygelius hybrida*
Varietal Denomination: Passionate

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/323,167

(22) Filed: Dec. 30, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Phygelius* plant named 'Passionate', characterized by its upright and somewhat outwardly spreading plant habit; freely flowering habit; dark green-colored foliage; and large bright red-colored flowers.

2 Drawing Sheets

Botanical designation: *Phygelius hybrida.*
Cultivar denomination: 'Passionate'.

BACKGROUND OF THE INVENTION

The present Invention relates to a new and distinct cultivar of *Phygelius* plant, botanically known as *Phygelius hybrida,* and hereinafter referred to by the cultivar name Passionate.

The new *Phygelius* is a product of a planned breeding program conducted by the Inventor in Lisserbroek, The Netherlands. The objective of the breeding program is to create new freely flowering *Phygelius* with attractive flower coloration.

The new *Phygelius* originated from a cross-pollination made by the Inventor in Lisserbroek, The Netherlands in 2002, of two unnamed selections of *Phygelius hybridus,* not patented. The new *Phygelius* was discovered and selected as a single plant from the resulting progeny of the cross-pollination in a controlled environment in Lisserbroek, The Netherlands in 2004.

Asexual reproduction of the new cultivar by softwood cuttings since 2004, in Lisserbroek, The Netherlands has shown that the unique features of this new *Phygelius* are stable and reproduced true to type in successive generations.

SUMMARY OF THE INVENTION

Plants of the cultivar Passionate have not been observed under all possible environmental conditions. The phenotype may vary somewhat with variations in environment such as temperature and light intensity without, however, any variance in genotype.

The following traits have been repeatedly observed and are determined to be the unique characteristics of 'Passionate'. These characteristics in combination distinguish 'Passionate' as a new and distinct cultivar:

1. Upright and somewhat outwardly spreading plant habit.
2. Freely flowering habit.
3. Dark green-colored foliage.
4. Large bright red-colored flowers.

Plants of the new *Phygelius* differ primarily from plants of the parent selections in flower color.

Plants of the new *Phygelius* can be compared to plants of the cultivar Blaphy, disclosed in U.S. Plant Pat. No. 13,464. In side-by-side comparisons conducted in Lisserbroek, The Netherlands, plants of the new *Phygelius* differed from plants of the cultivar Blaphy in the following characteristics:

1. Plants of the new *Phygelius* were more compact than plants of the cultivar Blaphy.
2. Plants of the new *Phygelius* and the cultivar Blaphy differed in flower color as plants of the cultivar Blaphy had red purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Phygelius.*

The photograph on the first sheet comprises a side perspective view of a typical plant of 'Passionate' grown in an outdoor nursery.

The photograph at the top of the second sheet is a close-up view of typical flowers of 'Passionate'.

The photograph at the bottom of the second sheet is a close-up view of a typical leaf of 'Passionate'.

DETAILED BOTANICAL DESCRIPTION

Plants of the cultivar Passionate have not been observed under all possible environmental conditions. The phenotype may vary somewhat with variations in environment such as temperature and light intensity, without, however, any variance in genotype. The aforementioned photographs and following observations and measurements describe plants grown during the summer in Roelofarendsveen, The Netherlands, under commercial practice in an outdoor nursery with day temperatures ranging from 18° C. to 32° C. and night temperatures ranging from 10° C. to 18° C. Plants used for the photographs and description were about two years old. In the following description, color references are made to The Royal Horticultural Society Colour Chart, 2001 Edition, except where general terms of ordinary dictionary significance are used.

Botanical classification: *Phygelius hybrida* cultivar Passionate.

Parentage:

*Female parent.*—Unnamed selection of *Phygelius hybrida,* not patented.

*Male parent.*—Unnamed selection of *Phygelius hybrida,* not patented.

Propagation:

*Type cutting.*—Softwood cuttings.

*Time to initiate roots.*—About four to five weeks at 15° C.

*Root description.*—Fine, fibrous; gray white in color.

*Rooting habit.*—Freely branching; dense.

Plant description:

*Form.*—Perennial flowering plant; upright and somewhat outwardly spreading plant habit. Freely basal branching habit; about eleven lateral branches per plant.

*Plant height.*—About 65 cm.

*Plant diameter.*—About 41 cm.

*Vigor.*—Moderately vigorous.

*Lateral branches.*—Length: About 18.4 cm. Diameter: About 3 mm. Internode length: About 4.3 cm. Texture: Smooth, glabrous. Color: Between N186C and 200A.

*Foliage description.*—Arrangement: Opposite, simple. Length: About 7.2 cm. Width: About 3 cm. Shape: Narrowly ovate. Apex: Acute. Base: Attenuate. Margin: Serrate. Texture, upper and lower surfaces: Smooth, glabrous. Venation pattern: Pinnate. Color: Developing leaves, upper surface: Slightly darker than 147A. Developing leaves, lower surface: 147B. Fully expanded leaves, upper surface: Between 139A and 147A, but much darker. Fully expanded leaves, lower surface: 146A. Venation, upper surface: N186C. Venation, lower surface: N186C to 187A. Petiole length: About 1.8 cm. Petiole diameter: About 2 mm. Petiole texture, upper and lower surfaces: Smooth, glabrous. Petiole color, upper and lower surfaces: N186C.

Flower description:

*Flower type and habit.*—Single salverform flowers arranged in terminal panicles. Freely flowering habit, usually about 60 flowers per panicle. Flowers pendulous. Flowers not persistent. Flowers not fragrant.

*Natural flowering season.*—Flowering continuous from late July to late September in The Netherlands. Plants start flowering about nine months after planting.

*Flower longevity.*—Flowers last about one week on the plant.

*Inflorescence length.*—About 31.9 cm.

*Inflorescence width.*—About 14.5 cm.

*Flower diameter.*—About 1.5 cm.

*Flower depth.*—About 5.3 cm.

*Flower buds.*—Length: About 2.8 cm. Diameter: About 6 mm. Shape: Narrowly oblong to obovate. Color: 39A; towards the apex, darker than 39A.

*Corolla.*—Shape/arrangement: Tubular; five fused petals. Petal apices: Broadly acute. Petal margin: Entire. Petal length: About 4 cm. Petal width: About 5 mm. Texture, upper and lower surfaces of petal lobes: Smooth, glabrous. Color: When opening and fully opened, inner surface: Tube, 11C; towards the apex, 6C; at the apex, 43A. When opening and fully opened, outer surface: 39A.

*Calyx.*—Length: About 6 mm. Diameter: About 1.1 cm. Shape: Campanulate. Sepal apex: Acute. Sepal margin: Entire. Sepal texture, upper and lower surfaces: Smooth, glabrous. Color, upper surface: N199A. Color, lower surface: 200B.

*Peduncles.*—Length: About 31.9 cm. Diameter: About 4 mm. Strength: Strong. Angle: Primary flowering stems, erect; secondary flowering stems, about 55° from the stem. Color: Between N186C and 200A.

*Pedicels.*—Length: About 1.8 cm. Diameter: About 1 mm. Strength: Strong. Angle: About 35° from the stem. Color: Between N186C and 200A.

*Reproductive organs.*—Androecium: Stamen quantity: Four per flower. Filament length: About 1.5 cm. Anther length: About 3 mm. Anther shape: Oval. Anther color: Between 147A and 201B. Pollen amount: Moderate. Pollen color: Darker than 195A. Gynoecium: Pistil quantity: One per flower. Pistil length: About 5.3 cm. Style length: About 5.2 cm. Style color: 39A. Stigma color: N200A. Ovary color: 146C.

*Seeds/fruits.*—Seed and fruit development has not been observed.

Disease/pest resistance: Plants of the new *Phygelius* have not been observed to be resistant to pathogens and pests common to *Phygelius.*

Temperature tolerance: Plants of the new *Phygelius* have been observed to tolerate temperatures from about 0° C. to 35° C.

It is claimed:

1. A new and distinct cultivar of *Phygelius* plant named 'Passionate', as illustrated and described.

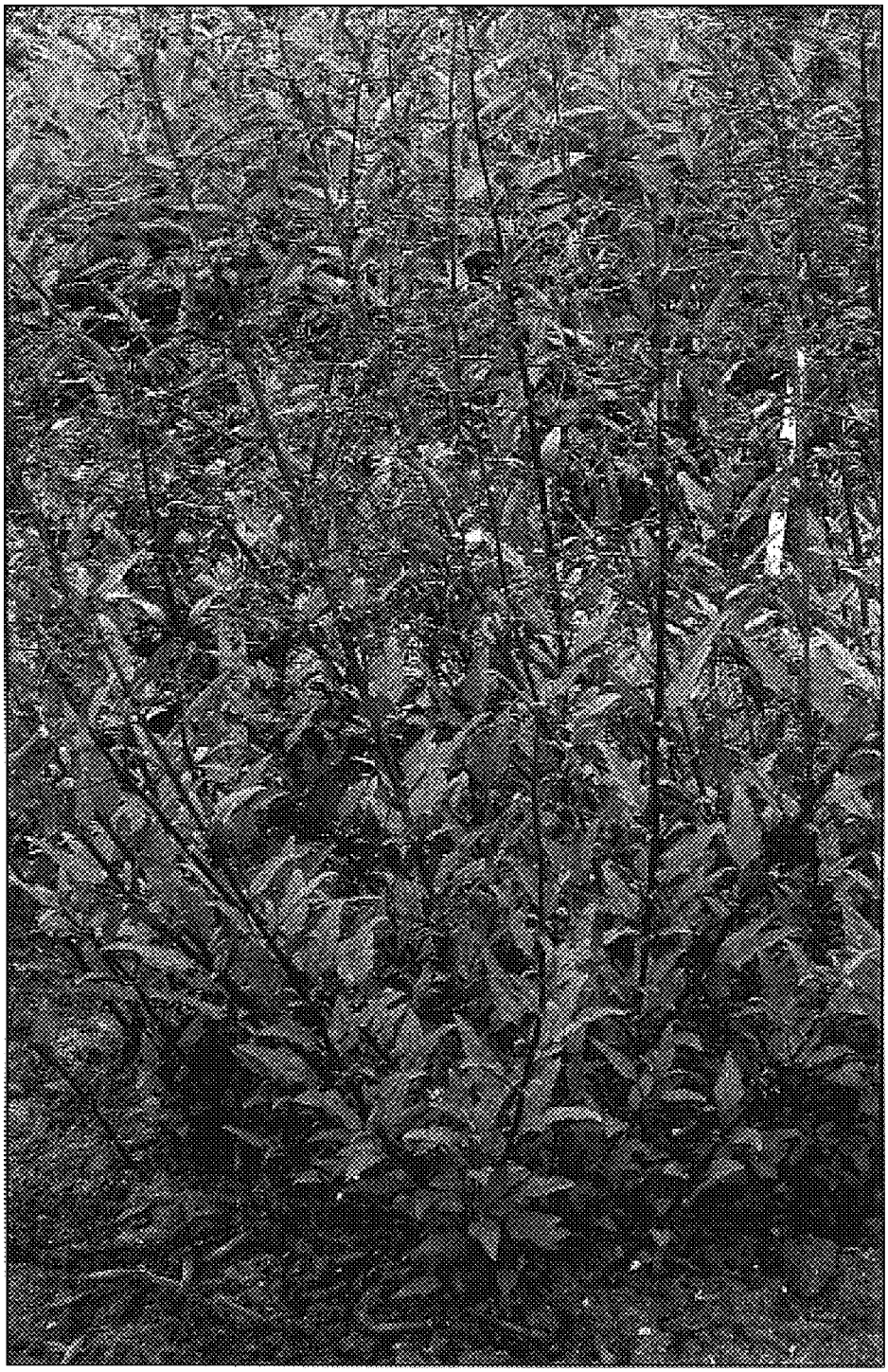

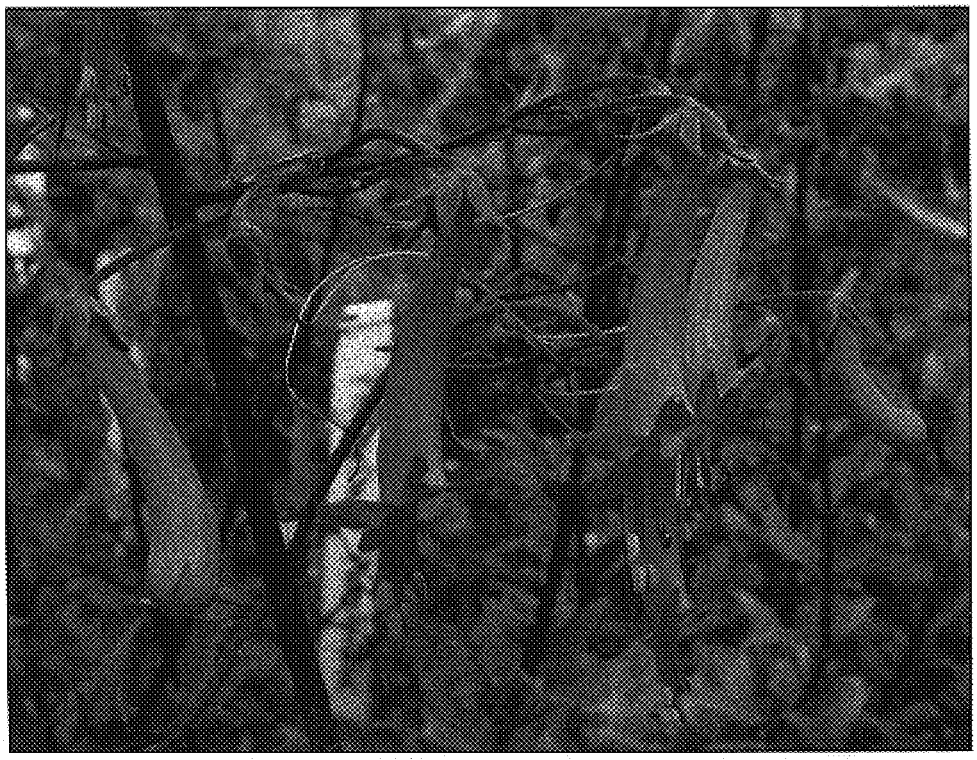
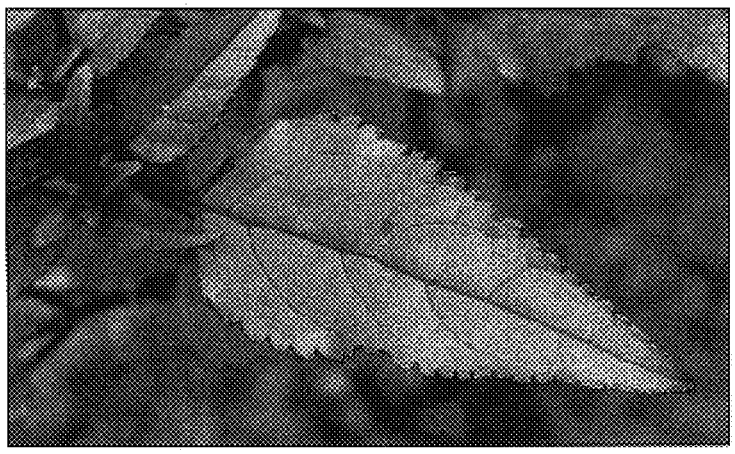

* * * * *